United States Patent
Yamamori et al.

(10) Patent No.: US 8,915,861 B2
(45) Date of Patent: Dec. 23, 2014

(54) ADAPTOR FOR COLLECTING EXPIRATORY INFORMATION AND BIOLOGICAL INFORMATION PROCESSING SYSTEM USING THE SAME

(75) Inventors: Shinji Yamamori, Tokyo (JP); Noriaki Tadokoro, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 1480 days.

(21) Appl. No.: 12/045,303

(22) Filed: Mar. 10, 2008

(65) Prior Publication Data
US 2009/0069646 A1    Mar. 12, 2009

(30) Foreign Application Priority Data

Mar. 9, 2007  (JP) .................. 2007-061006
Dec. 27, 2007 (JP) .................. 2007-336001

(51) Int. Cl.
| | | |
|---|---|---|
| A61B 5/08  | (2006.01) | |
| A61B 5/097 | (2006.01) | |
| A61B 5/083 | (2006.01) | |
| A61B 5/00  | (2006.01) | |

(52) U.S. Cl.
CPC ............ *A61B 5/097* (2013.01); *A61B 5/0836* (2013.01); *A61B 5/4818* (2013.01); *A61B 5/6819* (2013.01); *A61B 5/682* (2013.01)
USPC .......................................... 600/532; 600/538

(58) Field of Classification Search
USPC ................... 600/529, 532, 538, 543
See application file for complete search history.

(56) References Cited

U.S. PATENT DOCUMENTS

| | | | | |
|---|---|---|---|---|
| 5,046,491 | A  | * | 9/1991  | Derrick .................. 128/200.24 |
| 5,056,513 | A  | * | 10/1991 | Boutin ................... 128/204.23 |
| 6,017,315 | A  | * | 1/2000  | Starr et al. ................. 600/538 |
| 6,155,986 | A  | * | 12/2000 | Brydon et al. .............. 600/538 |
| 2001/0031929 | A1 | * | 10/2001 | O'Toole ..................... 600/532 |
| 2002/0055685 | A1 | * | 5/2002  | Levitsky et al. ............ 600/543 |
| 2003/0199780 | A1 | * | 10/2003 | Page .......................... 600/538 |
| 2004/0206907 | A1 | * | 10/2004 | Yamamori et al. ......... 250/343 |
| 2005/0284484 | A1 |   | 12/2005 | Curti et al. |
| 2006/0130840 | A1 | * | 6/2006  | Porat et al. ............. 128/206.11 |
| 2007/0113847 | A1 | * | 5/2007  | Acker et al. ............ 128/204.18 |
| 2009/0275851 | A1 | * | 11/2009 | Colman et al. ............. 600/532 |

FOREIGN PATENT DOCUMENTS

| | | |
|---|---|---|
| JP | 11-267223 A | 10/1999 |
| JP | 2004-321721 A | 11/2004 |

* cited by examiner

*Primary Examiner* — Navin Natnithithadha
*Assistant Examiner* — Michael R Bloch
(74) *Attorney, Agent, or Firm* — Sughrue Mion, PLLC (57) ABSTRACT

An adaptor is adapted to be attached on a face of the subject to collect expiration gas of the subject. An airway case is formed with a chamber, and adapted to be coupled with a carbon dioxide sensor so that carbon dioxide in the expiration gas flowing through the chamber is detected by the carbon dioxide sensor. Nasal tubes are adapted to be inserted into nostrils of the subject when the adaptor is attached on the face of the subject. The nasal tubes are adapted to lead nasal expiration gas of the subject to the chamber. A mouth guide is adapted to lead oral expiration gas of the subject to the chamber when the adaptor is attached on the face of the subject. A branch tube is communicating with the nasal tubes and adapted to lead pressure generated by the nasal expiration gas to an external pressure sensor.

6 Claims, 10 Drawing Sheets

ADAPTOR FOR COLLECTING EXPIRATORY INFORMATION AND BIOLOGICAL INFORMATION PROCESSING SYSTEM USING THE SAME

BACKGROUND

The present invention relates to an adaptor for collecting expiratory information capable of measuring carbon dioxide concentration from both nasal expiration gas and oral expiration gas of one subject, and of measuring airflow pressure of the nasal expiration gas.

The present invention also relates to a biological information processing system using such an adaptor.

In recent years, a steep condition has been particularly examined to check a driver's health in view of safety in various transportation facilities. That is, in many cases, an examination of a sleep apnea syndrome (SAS) is carried out. In order to examine the sleep apnea syndrome, respirations are detected by measuring airflow pressure together with various parameters through the use of a nasal cannula. Recently, in addition to the respiration detection, an activity of a respiratory center and an amount of carbon dioxide tension in a body have been examined by measuring carbon dioxide concentration in expiration.

As a technique for measuring the carbon dioxide concentration in expiration, Japanese Patent Publication No. 11-267223A teaches that nasal tubes inserted into nostrils are connected to a tube for collecting oral expiration gas at a connecting portion, and a side-stream type capnometer samples respiratory gas from the connecting portion. Further, Japanese Patent Publication No. 2004-321721A discloses a device configured such that nasal expiration gas and oral expiration gas are lead to a small-sized carbon dioxide sensor disposed right below nostrils.

However, in the above techniques, it is possible to measure carbon dioxide concentration of expiration, but it is not possible to measure airflow pressure at the same time. Additionally, in the disclosed devices, it is possible to measure carbon dioxide concentration of nasal expiration gas or oral expiration gas, but it is not possible to distinguish the nasal expiration gas and the oral expiration gas.

In addition, United States Published Application No. 2005/0284484 A1 discloses a device for measuring both airflow pressure and carbon dioxide. This device is configured such that a nasal cannula is divided into left and right spaces by a partition wall so as to measure carbon dioxide in one space and to measure airflow pressure in other space. However, in the device disclosed in this publication, since expiration is individually used while being extracted from each of left and right nostrils, information on only one nostril is obtained at the time one nostril is blocked, and thus there would be a case that satisfactory examination cannot be performed.

In addition to the above techniques, a tube for collecting nasal expiration gas and a tube for collecting carbon dioxide may be separately provided and both are inserted into the respective nostrils. However, particularly, in a case where a subject is a child, it is burdensome to insert two types of tubes into the nostrils.

SUMMARY

It is therefore one advantageous aspect of the invention to provide a small-sized adaptor for collecting expiratory information capable of measuring not only carbon dioxide concentration of the nasal expiration gas and the oral expiration gas but also the airflow pressure, thereby reducing a subject's burden.

It is also one advantageous aspect of the invention to provide an adaptor for collecting expiratory information capable of distinguish the nasal respirations and the oral respirations.

It is also one advantageous aspect of the invention to provide a biological information processing system using such an adaptor.

In order to achieve the above objects, according to one aspect of the invention, there is provided an adaptor, adapted to be attached on a face of the subject to collect expiration gas of the subject, comprising:

an airway case, formed with a chamber, and adapted to be coupled with a carbon dioxide sensor so that carbon dioxide in the expiration gas flowing through the chamber is detected by the carbon dioxide sensor;

nasal tubes, adapted to be inserted into nostrils of the subject when the adaptor is attached on the face of the subject, the nasal tubes adapted to lead nasal expiration gas of the subject to the chamber;

a mouth guide adapted to lead oral expiration gas of the subject to the chamber when the adaptor is attached on the face of the subject; and a branch tube, communicating with the nasal tubes and adapted to lead pressure generated by the nasal expiration gas to an external pressure sensor.

With this configuration, it is possible to measure not only carbon dioxide concentration of the nasal expiration gas and the oral expiration gas but also the airflow pressure at the same time with a small-sized configuration. Additionally, since only the nasal tubes are inserted into the nostrils, the subject will not be strained.

The branch tube may be extended from each of the nasal tubes. A wall may be adapted to branch the nasal expiration gas into one led to the airway case and one led to the branch tube when the nasal tubes are inserted into the nostrils.

The wall may be formed with a flow direction regulator adapted to lead the pressure to the branch tube, when the adaptor is attached to the face of the subject.

A tip end of the branch tube may be disposed within each of the nasal tubes and directed upward when the adaptor is attached on the face of the subject, so that a part of an outer face of the branch tube blocks the oral expiration gas.

In this case, since airflow pressure cannot be detected during oral respirations, it is possible to distinguish between nasal expiration gas and oral expiration gas.

In the case where the branch tube is provided on each of the nasal tubes, even when one nostril, one nasal tube, or one branch tube is clogged, it is possible to appropriately measure the airflow pressure.

Proximal ends of the nasal tubes may be integrated to form a joint portion. The branch tube may be coupled with the joint portion. The joint portion may be formed with a flow direction regulator adapted to guide the part of the nasal expiration gas to the branch tube white blocking the oral expiration gas, when the adaptor is attached to the face of the subject.

According to one aspect of the invention, there is provided a biological information processing system, comprising:

a carbon dioxide sensor, adapted to detect carbon dioxide in expiration gas of a subject;

a pressure sensor, adapted to detect airflow pressure of nasal expiration gas of the subject;

an adaptor, adapted to be attached on a face of the subject and comprising:

an airway case, adapted to be coupled with the carbon dioxide sensor and formed with a chamber, so that carbon dioxide concentration in the expiration gas flowing through the chamber is measured by the carbon dioxide sensor;

nasal tubes, adapted to be inserted into nostrils of the subject when the adaptor is attached on a face of the subject, the nasal tubes adapted to lead nasal expiration gas of the subject to the chamber;

a mouth guide adapted to lead oral expiration gas of the subject to the chamber when the adaptor is attached on the face of the subject; and a branch tube, communicating with the nasal tubes and adapted to lead pressure generated by the nasal expiration gas to the pressure sensor.

DETAILED DESCRIPTION OF EXEMPLARY EMBODIMENTS

Exemplary embodiments of the invention will be described below in detail with reference to the accompanying drawings. Similar components will be designated by same reference numerals and repetitive explanations for those will be omitted.

Figure 1:
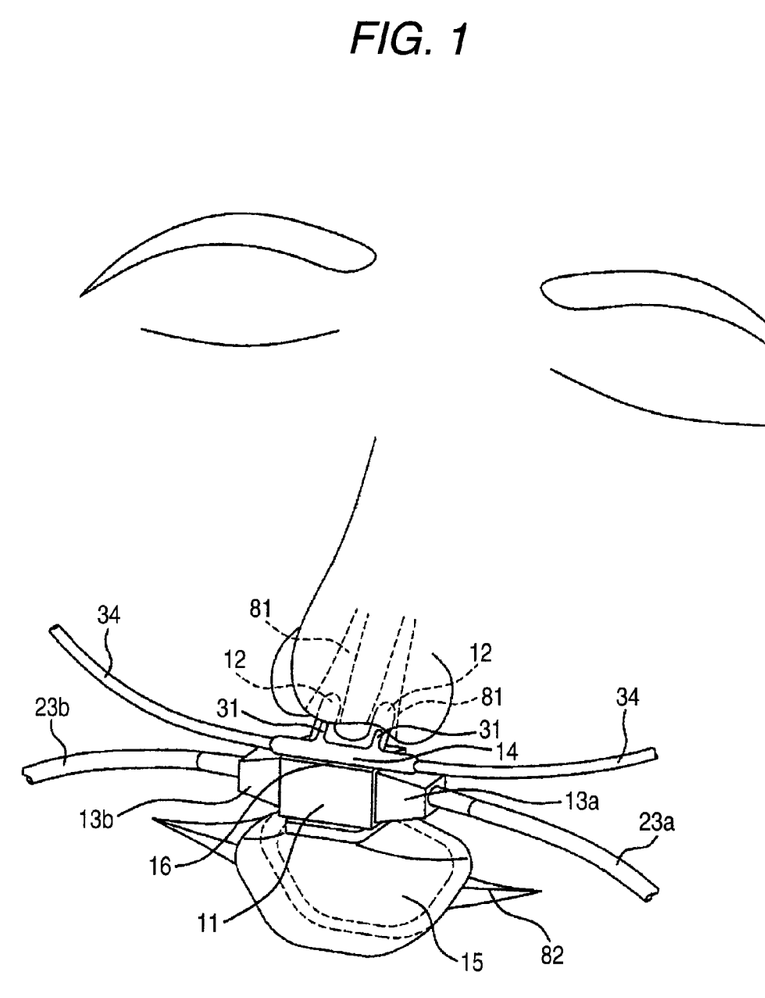
FIG. 1 is a perspective view showing a state that an adaptor for collecting expiratory information according to a first embodiment of the invention is attached to a subject.
Figure 2:
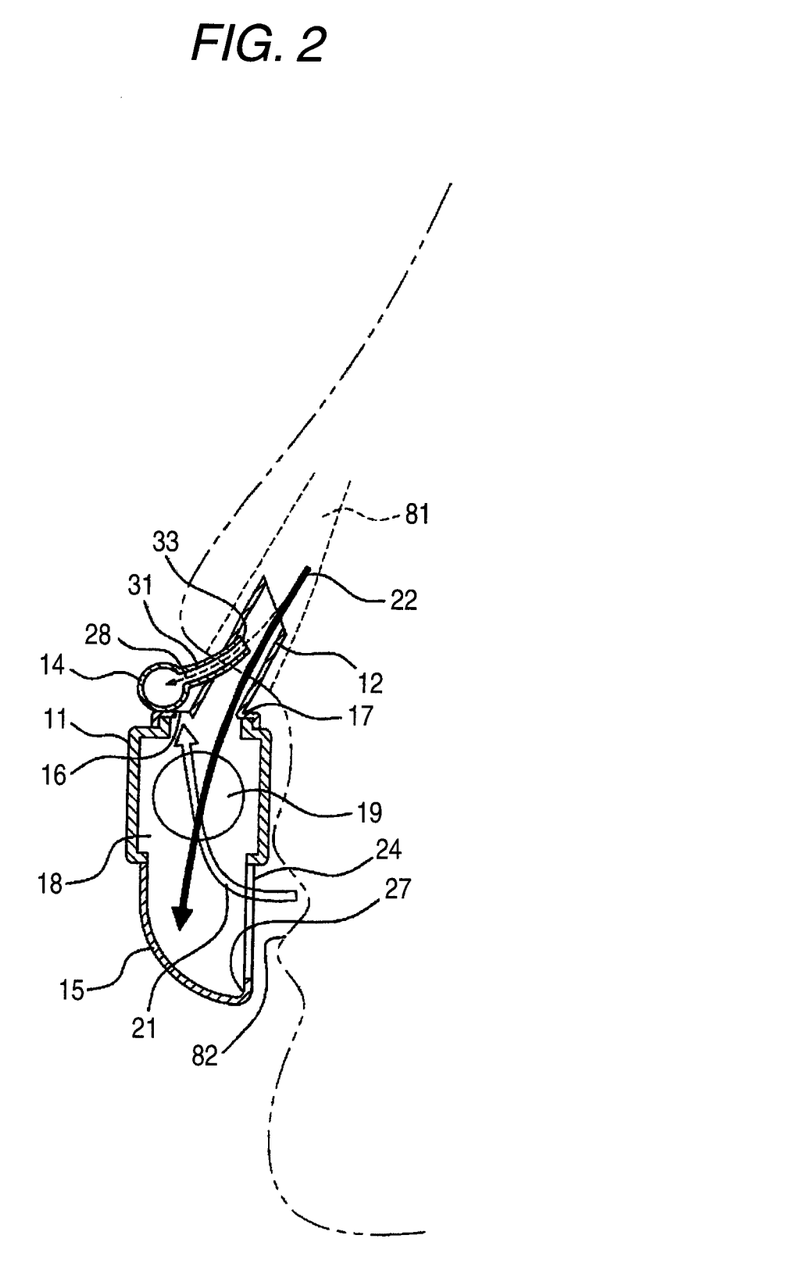
FIG. 2 is a longitudinal section view of the adaptor of FIG. 1.

FIGS. 1 and 2 illustrate an adaptor for collecting expiratory information according to a first embodiment of the invention. The adaptor comprises a cubical airway case 11, nasal tubes 12, a carbon dioxide sensor 13 having a light emitting element 13a and a light receiving element 13b, a pressure cannula 14, and a mouth guide 15.

The airway case 11 is formed of resin, which is not flexible, and a through hole 16 is formed at the front of a top portion thereof in use so as to send out oral expiration gas 21. Additionally, a base 17 of the nasal tubes 12 is fitted to the back of the through hole 16 of the airway case 11, and the nasal expiration gas 22 is introduced from nostrils 81 into a chamber 18 of the airway case 11. The nasal tubes 12 are formed of flexible resin such as a silicon rubber. The two nasal tubes 12 are inserted into both nostrils 81. The two nasal tubes 12 are integrally formed with the base 17.

One side portion of the airway case 11 is connected to the light emitting element 13a, and the other side portion thereof is connected to the light receiving element 13b. Windows 19 serving a light emitting surface of the light emitting element 13a and a light receiving surface of the light receiving element 13b are opposed to each other while sandwiching the chamber 18 therebetween. Lead lines 23a and 23b are connected to the light emitting element 13a and the light receiving element 13b, respectively, so as to extend up to a measurement device.

The mouth guide 15 is suspended from the front of a bottom portion of the airway case 11 in use. In the bottom portion of the airway case 11 in use, the portion closer to a mouth 82 than the attachment position of the mouth guide 15 is an opening portion 24, and the oral expiration gas 21 is introduced from the mouth 82 into the chamber 18 of the airway case 11 through the opening portion 24 so as to be sent out through the through hole 16. The mouth guide 15 is formed of flexible resin such as poly-vinyl chloride, and a circumference edge 27 is curled inward. Accordingly, it is effective to collect the oral expiration gas 21 from the mouth 82.

The nasal tubes 12 are connected to two branch tubes 31, respectively. The branch tubes 31 are connected to the pressure cannula 14 so that the pressure generated by the nasal expiration (hereinafter, referred to as nasal expiration pressure 28) is led to a pressure sensor. Both sides of the pressure cannula 14 are attached to, for example, tubes 34 formed of poly-vinyl chloride.

As shown in FIG. 2, a tip end 33 of the branch tube 31 projects toward the nostrils 81 inside the nasal tubes 12. At this time, the tip end 33 has an opening adapted to oppose expiration flow, and serves to lead the nasal expiration pressure 28 to the branch tube 31 as a flow direction regulator.

As shown in FIGS. 1 and 2, in the adaptor configured as described the above, the nasal tubes 12 are inserted into both nostrils 81 of a subject, and then the mouth guide 15 is positioned at the mouth 82. At this time, some positions may be fixed to a face using an adhesive tape or the like if necessary. In this state, as shown in FIG. 2, the oral expiration gas 21 is introduced from the mouth 82 into the chamber 18 of the airway case 11 through the opening portion 24 so as to be sent out through the through hole 16. Additionally, the nasal expiration gas 22 is introduced from the nostril 81 to the chamber 18 of the airway case 11 through the nasal tubes 12 so as to be sent out through the opening portion 24 or the through hole 16.

The carbon dioxide contained in the oral expiration gas 21 and the nasal expiration gas 22 absorbs light emitted from the light emitting element 13a and changes light intensity that is received by the light receiving element 13b. Accordingly, a signal in accordance with the carbon dioxide concentration is obtained, and then is transmitted to the measurement device through the lead line 23b.

Additionally, the nasal expiration gas 22 from the nostril 81 collides with the tip end 33 of the branch tubes 31 projecting into the nasal tubes 12 so that the nasal expiration pressure 28 is led to the branch tubes 31. Subsequently, the nasal expiration pressure 28 reaches the pressure sensor through the pressure cannula 14 and the tubes 34.

Accordingly, it is possible to measure the carbon dioxide concentration on the basis of the nasal expiration gas 22 from the nostril 81 and the oral expiration gas 21 from the mouth 82, and it is possible to measure airflow pressure using the branch tubes 31 and the pressure cannula 14, thereby checking nasal expiration gas. On the other hand, since the tip end 33 of the branch tubes 31 is opened in a direction opposite to the flow direction of the oral expiration gas, the airflow pressure cannot be detected during only oral respirations are performed. Accordingly, it is possible to distinguish between nasal respirations and oral respirations, which were conventionally difficult to be distinguished.

Figure 3:
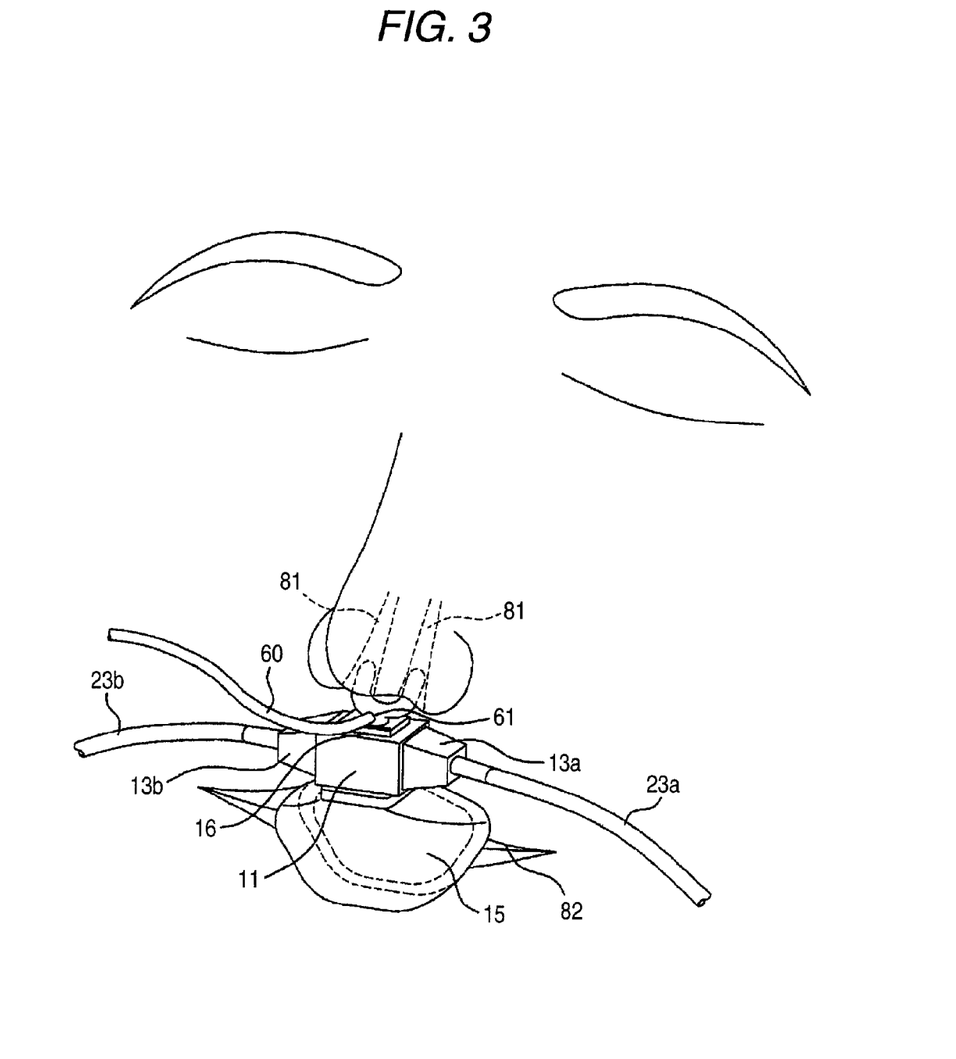
FIG. 3 is a perspective view showing a state that an adaptor for collecting expiratory information according to a second embodiment of the invention is attached to a subject.
Figure 4:
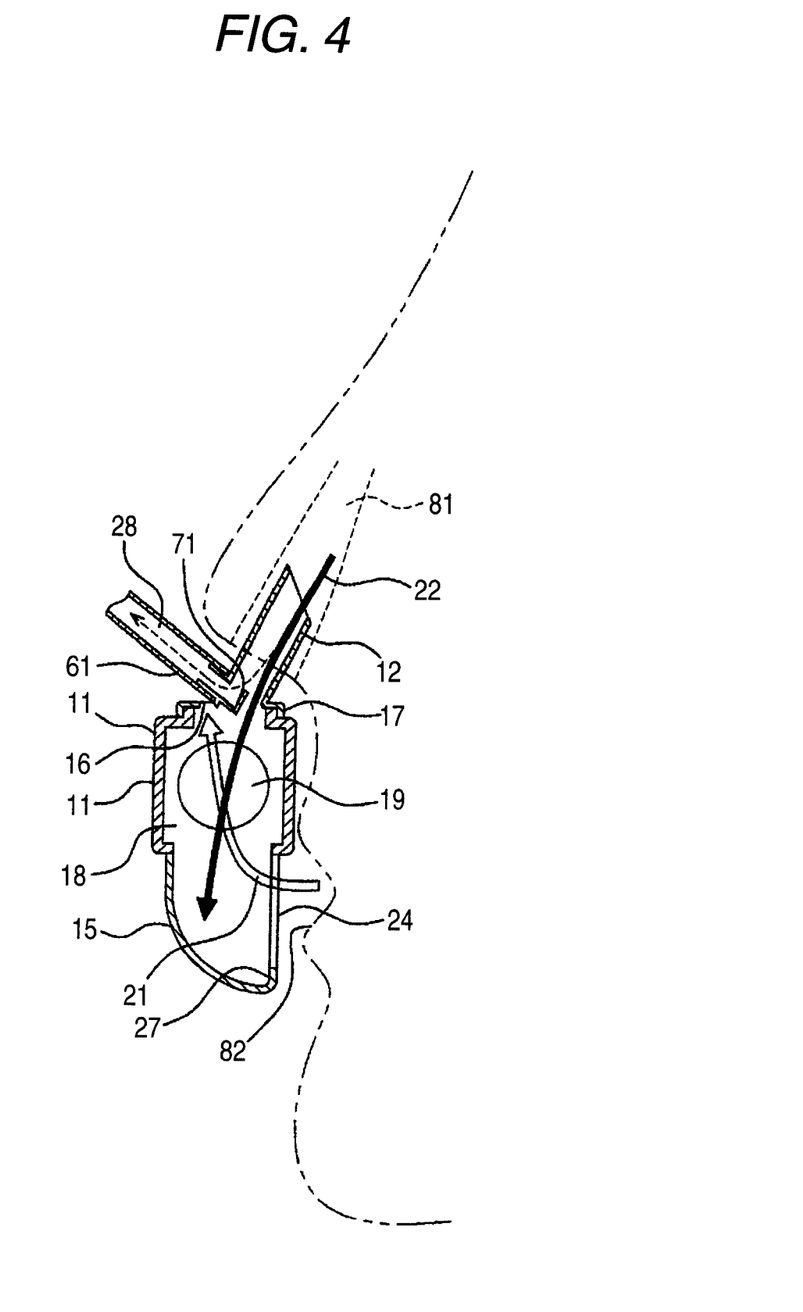
FIG. 4 is a longitudinal section view of the adaptor of FIG. 3.

FIGS. 3 and 4 illustrate an adaptor for collecting expiratory information according to a second embodiment of the invention. In this embodiment, one end of a pressure tube 60 serves as a branch tube 61. The tip end of the branch tube 61 (pressure tube 60) is connected to a downstream side (relative to nasal expiration gas flow) of a base 17 of nasal tubes 12, and a flow direction regulator 71 is formed inside the nasal tubes 12 at the part where the branch tube is connected. The flow direction regulator 71 has an L-shaped cross section, so that one end thereof is located at the center of the nasal tubes 12 and the other end thereof is brought into contact with an inner face of the branch tube 61. With this configuration, the nasal expiration pressure 28 is led to the pressure sensor by way of the pressure tube 60.

The other configurations are the same as those in the first embodiment. Accordingly, as shown in FIG. 4, the nasal expiration gas 22 from nostril 81 collides with the flow direction regulator 71 projecting into the nasal tubes 12 so that the nasal expiration pressure 28 is led to the branch tube 61. Subsequently, the nasal expiration pressure 28 is led to the pressure sensor by way of the pressure tube 60. With the above-described configurations, it is possible to obtain the same advantages as those of the first embodiment.

Figure 5:
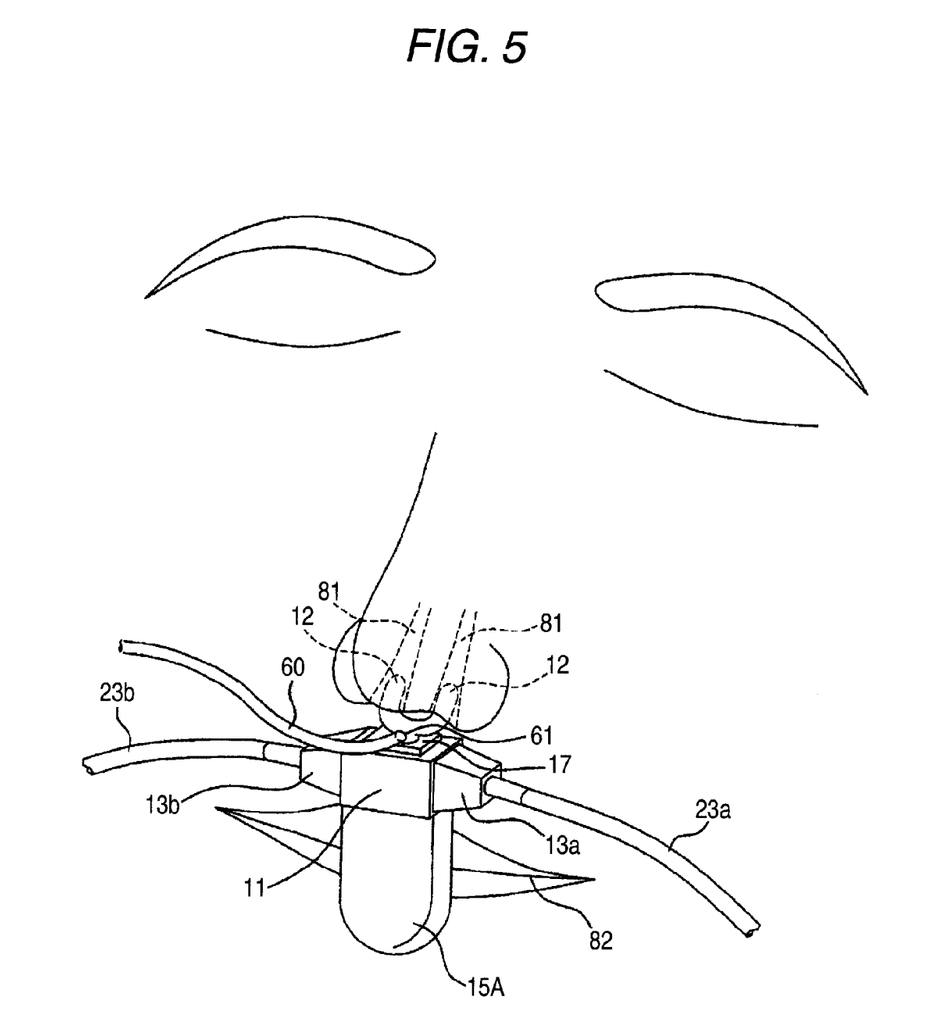
FIG. 5 is a perspective view showing a state that an adaptor for collecting expiratory information according to a modified example of the second embodiment is attached to a subject.

FIG. 5 illustrates a modified example of the adaptor according to the second embodiment. This example comprises a tongue-shaped mouth guide 15A so as to obtain expiration from the central portion of the mouth 82. This example is applicable to a case where a patient feels uncomfortable to take a breath while the whole portion of the mouth 82 is covered with the mouth guide 15. This configuration may be applicable with respect to the adaptor according to first embodiment.

Figure 6:
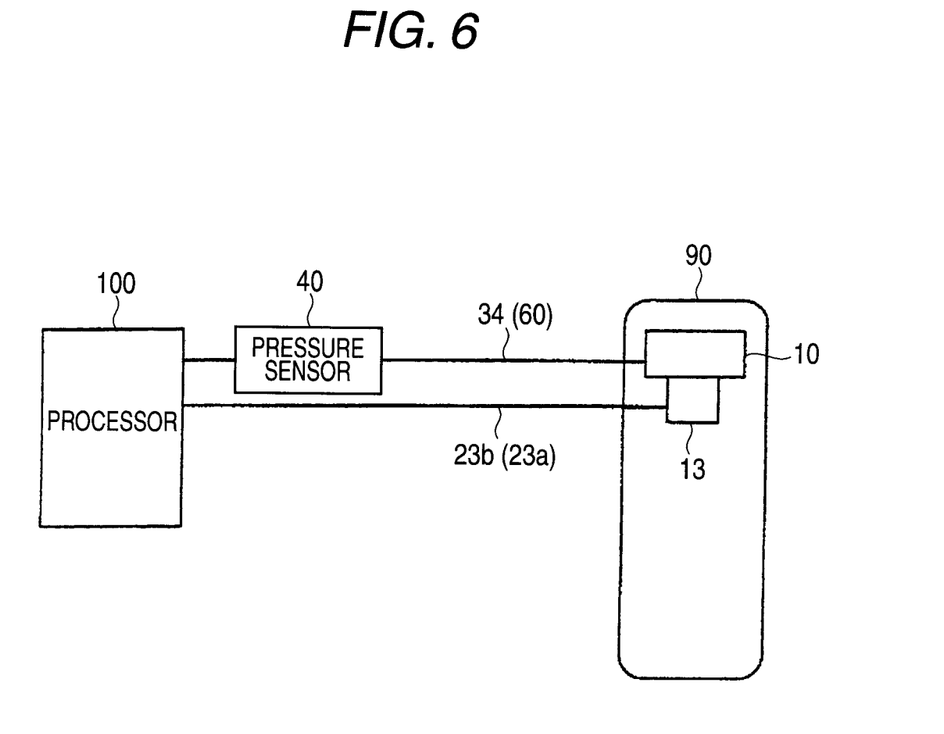
FIG. 6 is a schematic view showing a biological information processing system using the above adaptor.

FIG. 6 illustrates a configuration of a biological information processing system using the adaptor described the above. In the biological information processing system, the adaptor 10 having the carbon dioxide sensor 13 is attached to a subject 90. The nasal expiration pressure 28 is led to a pressure sensor 40 through the tubes 34 (60). Detection signals of the pressure sensor 40 and the carbon dioxide sensor 13 are sent to a processor 100.

The processor 100, for example, converts information on airflow pressure and carbon dioxide concentration into numerical values on the basis of the detection signals of the pressure sensor 40 and the carbon dioxide sensor 13, and outputs the information in the form of a time-sequential graph or the like. With such an output, the changes in the airflow pressure and the carbon dioxide concentration of the subject 90 can be visually checked. Accordingly, it is possible to distinguish the nasal respirations and the oral respirations, which were conventionally difficult to be distinguished.

Figure 7:
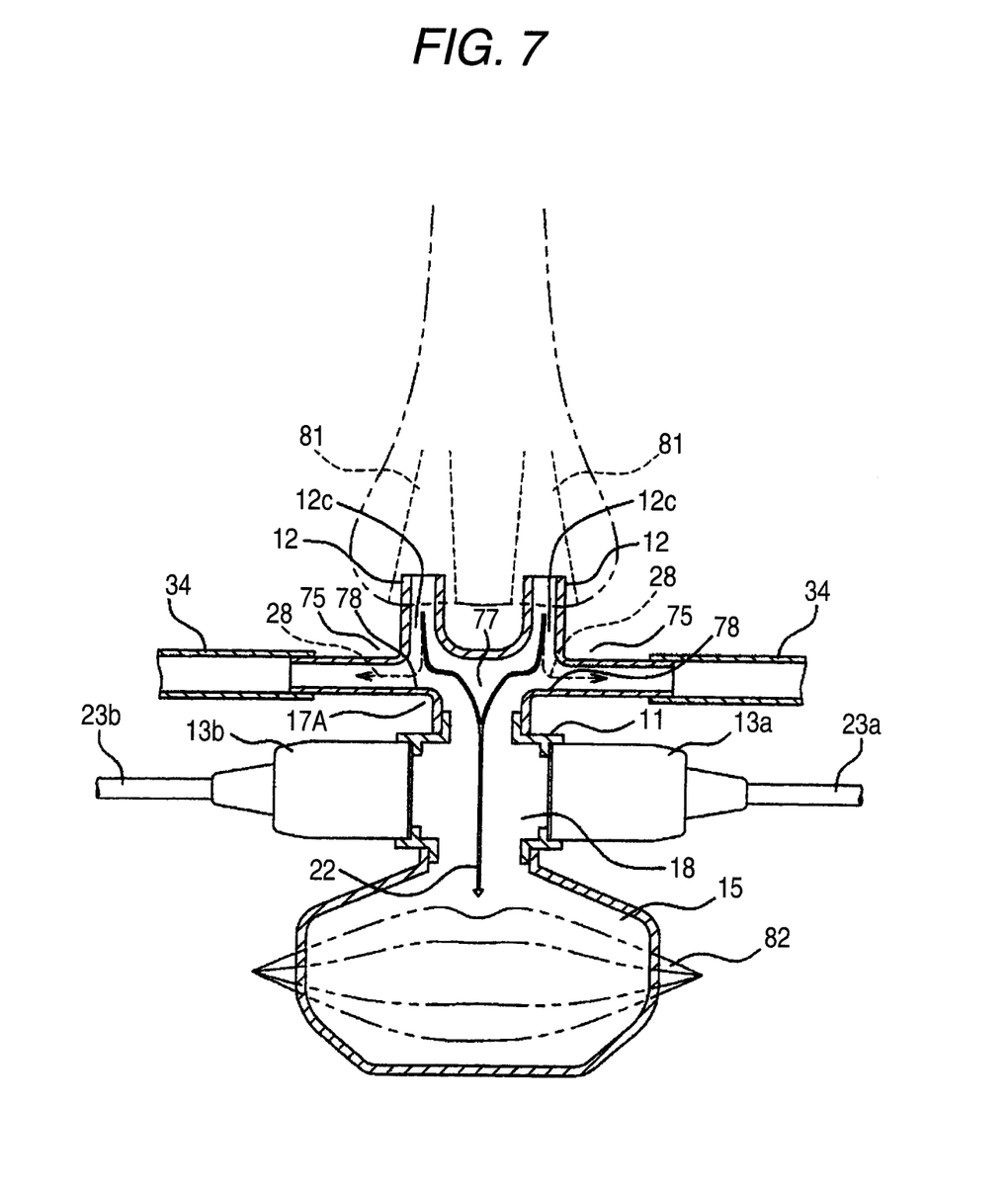
FIG. 7 is a perspective view showing a state that an adaptor for collecting expiratory information according to a third embodiment of the invention is attached to a subject.
Figure 8:
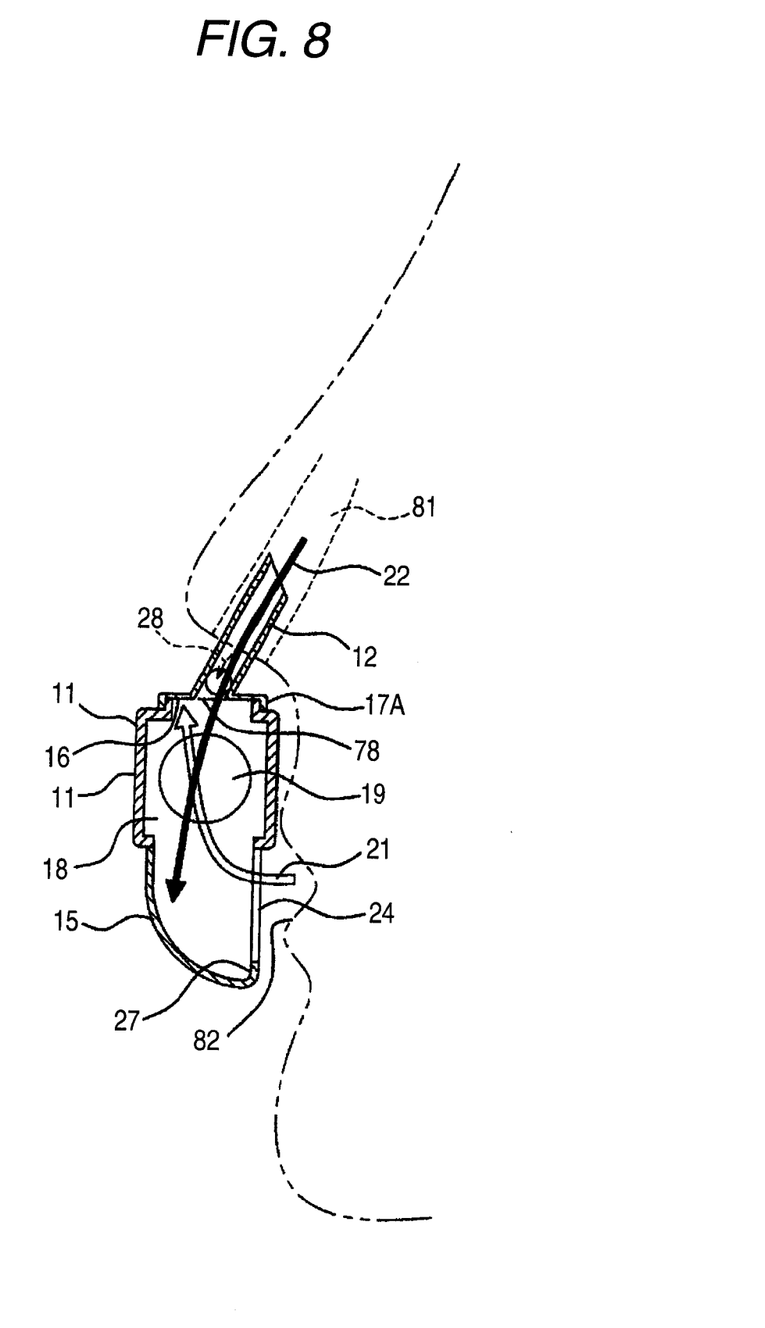
FIG. 8 is a longitudinal section view of the adaptor of FIG. 7.

FIGS. 7 and 8 illustrate an adaptor for collecting expiratory information according to a third embodiment of the invention. The adaptor is also applicable to the biological information processing system shown in FIG. 6. In this embodiment, cylindrical sleeves 75 are formed in bases 17A of nasal tubes 12 so as to extend perpendicularly to the nasal tubes 12 and to protrude leftward and rightward in use. Tubes 34 are fitted to the sleeves 75 and connected to a pressure sensor. The sleeves 75 serve as branch tubes for leading the nasal expiration pressure 28 to the tubes 34 so that the nasal expiration pressure 28 is led to the pressure sensor via the tubes 34.

Walls 78 are formed at positions where the nasal expiration gas 22 collides and so as to continue to parts of the sleeves 75, so that the nasal expiration pressure 28 is lead to the sleeves 75. As shown in FIG. 7, a flow passage 77 located at the center of the left and right sleeves 75 is connected to a chamber 18 of the airway case 11. Any other configurations in connection with the airway case 11 are the same as those in the first and second embodiments. With the above-described configurations, it is possible to obtain the same advantages as those in the first and second embodiments.

In this embodiment, the sleeves 75 extend substantially perpendicularly to the nasal tubes 12 and to protrude leftward and rightward in use. However, the directions that the sleeves 75 extend may be changed if the extending direction of the sleeves 75 intersects the extending direction of the nasal tubes 12, except such a direction that the tubes 34 extend toward a face of the subject or such a direction that causes the handling of the tubes 34 to be difficult. Further, the configuration shown in FIG. 5 may be applied to this embodiment.

Figure 9:
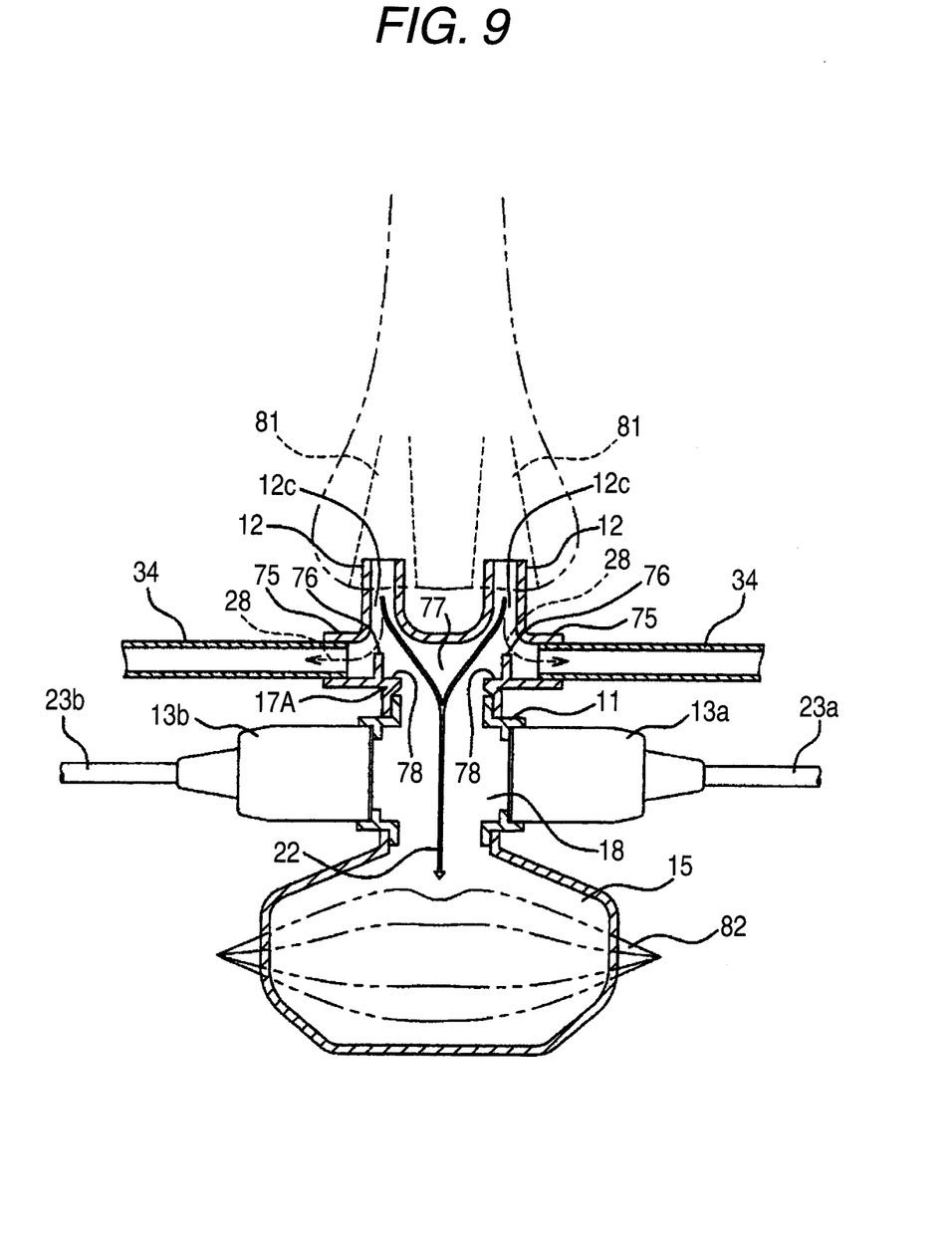
FIG. 9 is a perspective view showing a state that an adaptor for collecting expiratory information according to a modified example of the third embodiment is attached to a subject.
Figure 10:
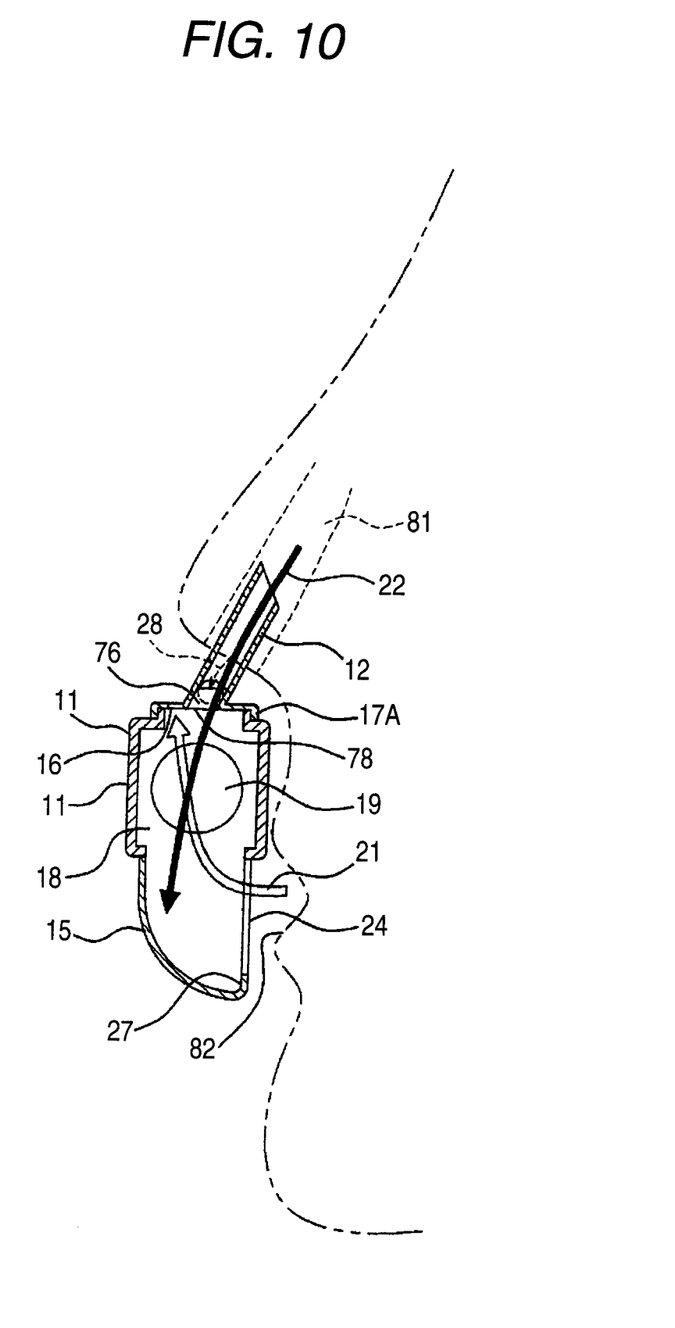
FIG. 10 is a longitudinal section view of the adaptor of FIG. 9.

FIGS. 9 and 10 illustrate a modified example of the third embodiment. This example is also applicable to the biological information processing system shown in FIG. 6.

This example is different from the third embodiment in that flow direction regulators 76 are formed with the walls 78 so as to extend toward center positions 12c of the nasal tubes 12. With this configuration, the flow direction of the nasal expiration gas 22 is regulated by the flow direction regulators 76 when the nasal expiration gas 22 collides with the walls 78, and then the nasal expiration pressure 28 is surely led to the sleeves 75. Accordingly, the nasal expiration pressure 28 is surely led to a pressure sensor through the tubes 34. Therefore, it is possible to obtain the same advantages as those in the above-described embodiments.

The flow direction regulators 76 may extend up to the inside of the nasal tubes 12, or may extend from the vicinity of the end portions of the nasal tubes 12 to the walls 78. The position, size, and height of the flow direction regulators 76 are appropriately determined by an expected amount of the nasal expiration pressure 28. Further, the configuration shown in FIG. 5 may be applied to this embodiment.

Although only some exemplary embodiments of the invention have been described in detail above, those skilled in the art will readily appreciated that many modifications are possible in the exemplary embodiments without materially departing from the novel teachings and advantages of the invention. Accordingly, all such modifications are intended to be included within the scope of the invention.

The disclosures of Japanese Patent Application Nos. 2007-61006 filed Mar. 9, 2007 and 2007-336001 filed Dec. 27, 2007 including specifications, drawings and claims are incorporated herein by reference in their entireties.

What is claimed is:

1. An adaptor, adapted to be attached on a face of the subject to collect expiration gas of the subject, the adaptor comprising:
   an airway case, formed with a chamber, and adapted to be coupled with a carbon dioxide sensor so that carbon dioxide in the expiration gas flowing through the chamber is detected by the carbon dioxide sensor;
   a mouth guide adapted to lead oral expiration gas of the subject to the chamber when the adaptor is attached on the face of the subject;
   nasal tubes, adapted to be inserted into nostrils of the subject when the adaptor is attached on the face of the subject, the nasal tubes form a first flow path through which a first portion of nasal expiration gas of the subject is fluidly communicated to the chamber and combined with the oral expiration gas in the chamber;
   a branch tube disposed proximate to the nasal tubes, which separates from the nasal tubes and forms a second flow path through which a second portion of nasal expiration gas of the subject is fluidly communicated from the nasal tubes to an external pressure sensor; and a flow direction regulator adapted to be positioned directly below the nostrils of the subject and including a projection projecting toward the nostrils of the subject when the adaptor is attached on the face of the subject, and configured to direct flow of the second portion of the nasal expiration gas on the second flow path from the nasal tubes to the external pressure sensor through the branch tube.

2. The adaptor as set forth in claim 1, wherein the branch tube is extended from each of the nasal tubes; and wherein the adaptor further comprises a wall configured to couple the branch tube to the nasal tubes.

3. The adaptor as set forth in claim 2, wherein:

the flow direction regulator extends from the wall towards the center of the nasal tubes.

4. The adaptor as set forth in claim 1, wherein:

a tip end of the branch tube is disposed within each of the nasal tubes and directed upward when the adaptor is attached on the face of the subject, so that a part of an outer face of the branch tube blocks the oral expiration gas.

5. The adaptor as set forth in claim 1, wherein:

proximal ends of the nasal tubes are integrated to form a joint portion;

the branch tube is coupled with the joint portion; and the joint portion is formed with the flow direction regulator adapted to guide the flow of the second portion of the nasal expiration gas to the branch tube while blocking the oral expiration gas, when the adaptor is attached to the face of the subject.

6. A biological information processing system, comprising:

a carbon dioxide sensor, adapted to detect carbon dioxide in expiration gas of a subject;

a pressure sensor, adapted to detect airflow pressure of nasal expiration gas of the subject; and an adaptor, adapted to be attached on a face of the subject and comprising:

an airway case, adapted to be coupled with the carbon dioxide sensor and formed with a chamber, so that the carbon dioxide in the expiration gas flowing through the chamber is detected by the carbon dioxide sensor;

a mouth guide adapted to lead oral expiration gas of the subject to the chamber when the adaptor is attached on the face of the subject;

nasal tubes, adapted to be inserted into nostrils of the subject when the adaptor is attached on a face of the subject, the nasal tubes forming a first flow path through which a first portion of nasal expiration gas of the subject is fluidly communicated to the chamber and combined with the oral expiration gas in the chamber;

a branch tube disposed proximate to the nasal tubes, which separates from the nasal tubes and forms a second flow path through which a second portion of the nasal expiration gas of the subject is fluidly communicated from the nasal tubes to the external pressure sensor; and a flow direction regulator adapted to be positioned directly below the nostrils of the subject and including a projection projecting toward the nostrils of the subject when the adaptor is attached on the face of the subject, and configured to direct flow of the second portion of the nasal expiration gas on the second flow path from the nasal tubes to the external pressure sensor through the branch tube.

* * * * *